United States Patent
Schnell et al.

[11] Patent Number: 6,051,134
[45] Date of Patent: Apr. 18, 2000

[54] BUBBLE TRAP HAVING COMMON INLET/OUTLET TUBE

[75] Inventors: William J. Schnell, Libertyville, Ill.; David S. Utterberg, Seattle, Wash.

[73] Assignee: Medisystems Technology Corporation, Seattle, Wash.

[21] Appl. No.: 09/320,295

[22] Filed: May 26, 1999

Related U.S. Application Data

[63] Continuation of application No. 08/829,546, Mar. 28, 1997, abandoned.

[51] Int. Cl.$^7$ .............................. B01D 19/00; A61M 1/00
[52] U.S. Cl. ........................... 210/188; 210/513; 96/204; 96/220; 604/4; 604/122
[58] Field of Search ................................. 210/188, 436, 210/512.1, 521; 95/260; 96/204, 220; 604/4, 122, 80; 422/44; 137/583

[56] References Cited

U.S. PATENT DOCUMENTS

| | | |
|---|---|---|
| 3,287,885 | 11/1966 | Sommer . |
| 3,342,019 | 9/1967 | Smythe . |
| 3,527,572 | 9/1970 | Urkiewicz . |
| 3,795,088 | 3/1974 | Esmond . |
| 3,908,653 | 9/1975 | Kettering . |
| 3,996,027 | 12/1976 | Schnell et al. . |
| 4,031,891 | 6/1977 | Jess . |
| 4,048,995 | 9/1977 | Mittleman . |
| 4,102,655 | 7/1978 | Jeffrey et al. ............................ 210/188 |
| 4,137,160 | 1/1979 | Ebling et al. . |
| 4,293,413 | 10/1981 | Schnell . |
| 4,311,137 | 1/1982 | Gerard . |
| 4,345,999 | 8/1982 | Sigdell et al. . |
| 4,493,705 | 1/1985 | Gordon et al. . |
| 4,531,937 | 7/1985 | Yates . |
| 4,568,333 | 2/1986 | Sawyer et al. . |
| 4,622,032 | 11/1986 | Katsura et al. . |
| 4,643,713 | 2/1987 | Viitala . |
| 4,666,598 | 5/1987 | Heath et al. . |
| 4,681,606 | 7/1987 | Swan, Jr. et al. . |
| 4,722,725 | 2/1988 | Sawyer et al. . |
| 4,722,731 | 2/1988 | Vailancourt . |
| 4,734,269 | 3/1988 | Clark et al. . |
| 5,061,236 | 10/1991 | Sutherland et al. . |
| 5,061,365 | 10/1991 | Utterberg . |
| 5,204,000 | 4/1993 | Steadman et al. . |
| 5,228,889 | 7/1993 | Cortial et al. . |
| 5,328,461 | 7/1994 | Utterberg . |
| 5,356,376 | 10/1994 | Milijasevic et al. . |
| 5,358,481 | 10/1994 | Todd et al. . |
| 5,411,705 | 5/1995 | Thor et al. . |
| 5,429,595 | 7/1995 | Wright, Jr. et al. . |
| 5,441,636 | 8/1995 | Chevallet et al. . |
| 5,520,640 | 5/1996 | Utterberg . |
| 5,591,251 | 1/1997 | Brugger . |
| 5,683,355 | 11/1997 | Fini et al. . |
| 5,830,185 | 11/1998 | Block, Jr. . |
| 5,980,741 | 11/1999 | Schnell et al. ........................... 210/188 |

FOREIGN PATENT DOCUMENTS

| | | |
|---|---|---|
| 0 058 325 | 8/1982 | European Pat. Off. . |
| 0 318 993 | 6/1989 | European Pat. Off. . |
| 0 350 675 | 1/1990 | European Pat. Off. . |
| 0 587 251 A1 | 3/1994 | European Pat. Off. . |
| 1 408 319 | 10/1975 | United Kingdom . |
| 1 544 810 | 4/1979 | United Kingdom . |

OTHER PUBLICATIONS

Medisystems Sales Drawing of Ready Set™ Bloodtubing Mar., 1993.

*Primary Examiner*—Joseph W. Drodge
*Attorney, Agent, or Firm*—Gerstman, Ellis & McMillian, Ltd.

[57] ABSTRACT

A flow through bubble trap comprises a chamber-defining wall having a flow inlet/outlet tube extending through the chamber and open at opposed tube ends. The tube has its bore closed with a partition, with ports in the side wall communicating with the chamber interior on opposite sides of the partition and adjacent to the bottom wall of the chamber.

31 Claims, 1 Drawing Sheet

BUBBLE TRAP HAVING COMMON INLET/OUTLET TUBE

CROSS REFERENCE TO RELATED APPLICATION

This is a Continuation of application Ser. No. 08/829,546 filed Mar. 28, 1997.

BACKGROUND OF THE INVENTION

Bubble traps used in blood lines for hemodialysis or the like conventionally comprise a typically rigid or semi-rigid tube in which a blood inlet is provided to convey blood into the top of the chamber, while a blood outlet draws blood from the bottom of the chamber. Bubbles then are given the opportunity to rise to the top of the chamber so that the blood in the bottom of the chamber, which is withdrawn to pass through another portion of the blood set, is relatively free of bubbles, since they migrate to the top of the chamber.

See also Utterberg U.S. Pat. Nos. 5,328,461 and 5,520,640 as other examples of bubble traps for blood lines known to the prior art.

Typically, such bubble traps are higher than they are wide, to provide a deep, vertical chamber for the blood so that bubbles are kept away from the bottom of the chamber, from which the blood is being withdrawn. Typically, the prior art bubble traps have chambers with a vertical height that is more than twice their width. The height of the chambers of the prior art, coupled with the buoyancy of the incoming bubbles, is intended to counteract the downward bulk fluid flow of blood in the chamber toward the bottom outlet.

The inlets of the prior art blood chambers are variably positioned, the idea being that the blood entering through such inlets, and the bubbles contained in the blood, will initially stay in an upper portion of the chamber so that the bubbles have time to migrate upwardly through a liquid level to a gas space at the top of the chamber. Some inlets are vertically oriented, extending downwardly from the top of the chamber. Because of the height of the chamber, inflowing blood stops moving downwardly before the bubbles contained in it can be caught in the outlet flow. Other inlets of the prior art are vertically oriented in the bottom of the chamber, to propel the inlet blood upwardly toward the chamber top. Other inlets are horizontally oriented in the side of the chamber, so that the inlet flow must horizontally cross the downward flow of the bulk blood in the chamber, moving to an opposite sidewall where it is turned upwardly. This raises the possibility of bubbles being entrained in the downward flow before they are turned upwardly to reach the intended air space.

The bubble trapping principles of the prior art are effective with large, buoyant bubbles, typically having a volume greater than 50 microliters, and at relatively low blood flow rates of less than 300 ml. per minute. Blood chambers for trapping bubbles typically have volumes of about 15–25 ml. The buoyancy of the bubbles urges them to the surface at a velocity greater than the downward velocity of the bulk flow of the fluid in the bubble trap.

However, such bubble traps are increasingly ineffective as bubbles get smaller, and/or as flow rates increase. Modern dialysis techniques often require blood flow rates exceeding 450 ml. per minute, which raises the risk that bubbles can get through bubble traps of the prior art.

To accommodate such higher flows, the volumes of some designs of prior art bubble traps have been increased. However, this is distinctly undesirable, since that increases the priming volume of the set. It is highly desirable to keep the priming volume of any blood set low, since it is important to minimize the amount of blood removed from a patient at any one time during a blood treatment procedure such as dialysis.

Furthermore, another problem of prior art bubble traps, particularly those with the upwardly oriented inlets, is that they may require a flow diverter, to prevent blood at high flow rate from bursting through the blood-gas interface in a geyser-like action, which causes foaming of the blood and consequent clotting in the chamber. A typical blood flow diverter comprises an indentation in the wall of the bubble trap, to force the upwardly moving stream of inlet blood into a more horizontal flow, to prevent such geyser-like action. However, the diverter itself is not deemed desirable, and may result in an increased number of bubbles to be driven down toward the bottom outlet and thus to pass out of the bubble trap, contrary to that which was intended.

In accordance with this invention, solutions to the above technical problems are provided, resulting in an improved flow-through bubble trap for blood lines or the like, which is capable of processing blood at high flow rates of 450 ml. per minute and greater, while still retaining a low chamber interior volume.

In Schnell and Utterberg application Ser. No. 08/755,806, filed Nov. 26, 1996, now abandoned, wide bubble traps are disclosed in which the width of the bubble trapping chamber is preferably wider that the height of the chamber. The fluid inlet and fluid outlet to these chambers are then laterally spaced from each other to provide a fluid flow pattern which typically is substantially horizontal in nature, with less of a vertical flow component than in the prior art. This has been found to facilitate the migration of bubbles upwardly to the top of the chamber.

DESCRIPTION OF THE INVENTION

By this invention, the principles of the above pending application may be used if and as desired, while the fluid inlet and fluid outlet to the chamber is arranged in a manner that permits a significant reduction in the size of the chamber. This, in turn, can result in a reduced blood volume in the chamber, which is a valuable improvement, with the invention also providing other significant improvements and advantages. The improved, flow-through bubble trap of this invention for blood lines or the like is capable of processing blood at high flow rates of 450 ml. or greater, while still retaining such a low chamber interior volume.

This invention pertains to a flow-through bubble trap for fluid flow lines and particularly blood flow lines. The bubble trap comprises a chamber formed by a chamber-defining wall of one or more connected pieces. A single or multiple component flow inlet/outlet tube at least substantially extends through the chamber, the tube being open at opposed tube ends for connection to other portions of a fluid flow set, for the conveying of blood or the like to and from a patient for hemodialysis or other treatment.

The flow inlet/outlet tube defines laterally facing flow inlet and flow outlet ports, each of which are defined to face laterally of the tube wall within the chamber interior. Also, the tube defines a partition closing the bore of the tube to substantially prevent direct flow between the flow inlet and flow outlet ports. Thus, a flow circuit is defined in which fluid enters one end of the tube and passes out of the tube into the chamber interior through the flow inlet port. Then, after circulation through the chamber, the fluid passes through the flow outlet port again into the tube, and continues its journey through the rest of the length of the tube. Short circuiting of fluid flow from this path is substantially prevented by the partition.

Preferably, the inlet and outlet ports of the tube are positioned adjacent to a bottom wall portion of the chamber-defining wall. The partition can extend substantially diagonally within the tube, also extending transversely to close the bore. Thus, various portions of the partition peripherally connect with the tube wall in positions which are longitudinally spaced from each other. This permits the flow inlet port and flow outlet port to be positioned at the same longitudinal level along the tube, while being separated from each other by the partition in the tube bore.

As described in the previously cited Schnell, Utterberg pending application, the chamber interior defined by the chamber-defining wall may have a height that is not substantially greater than the longest horizontal dimension of the chamber interior. In other words, the chamber interior height may preferably be no more than 1.2 times the longest horizontal dimension (width) of the chamber interior. Preferably, the chamber interior has a height that is less than the longest horizontal dimension thereof, so that the flow pattern of fluid within the chamber will have a substantially horizontal overall flow, and the vertical flow component is suppressed when compared with the flow patterns of the vertically extended bubble traps of the prior art.

One end of the flow inlet/outlet tube may be directly connected to a length of roller pump tubing as part of blood flow set, or to another kind of pump, to provide a compact assembly. A supplemental inlet port may be carried by the chamber-defining wall, communicating with a chamber interior at the end of the bubble trap which is adjacent to the roller pump tubing, shown to be the upper end of the bubble trap in the drawings below. The supplemental inlet port preferably extends transversely to the flow inlet/outlet tube, and may connect to a pressure monitor line. Such a transverse pressure monitor line port allows the chamber of this invention to be nested right next to a conventional pump housing of certain commercial hemodialysis machines while the pump tubing is carried in a roller pump assembly of the machine. If the pressure monitor line port was parallel to the central tube of the chamber, it would interfere with a close, nesting relation with the pump housing of such commercial hemodialysis apparatus.

The flow inlet/outlet tube is preferably spaced by at least about 7 mm. and typically about 9–10 mm. from side wall portions of the chamber-defining wall. The flow inlet/outlet tube may be a central tube extending centrally through a basically cylindrical chamber. The flow inlet port may face away from the flow outlet port. The flow inlet and outlet ports may occupy the same longitudinal position along the flow inlet/outlet tube, to provide a swirling inlet and outlet flow through the interior of the chamber that has a substantial horizontal flow component, thus permitting bubbles to rise to the top wall of the chamber and remain there without being swept onward in the flow circuit. This is accomplished with a low volume chamber, having a volume of typically 15 to 30 cc., while still effectively removing bubbles even at high flow rates of at least 450 cc. per minute and the like.

The chamber of this invention can be used in a "prepump" or a "post pump" mode. It is effective for bubble removal with flow in either direction through the chamber. It may also be used as a venous chamber, as well as an arterial chamber, by the typical application of a filter in the flow outlet of the chamber.

DESCRIPTION OF SPECIFIC EMBODIMENTS

Referring to FIGS. 1–6, a flow through bubble trap 10 is disclosed, being typically used as part of arterial or venous blood sets for the circulation of blood between a patient and a blood treatment device, for example as in hemodialysis. Such blood sets of the prior art are manufactured and sold by the Medisystems Corporation of Seattle, Wash., among others.

Figure 1:
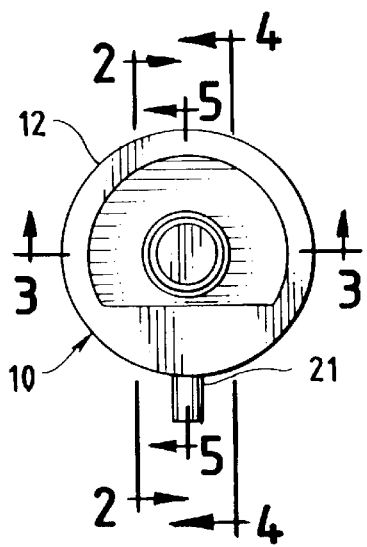
FIG. 1 is a top plan view of the chamber of this invention.
Figure 2:
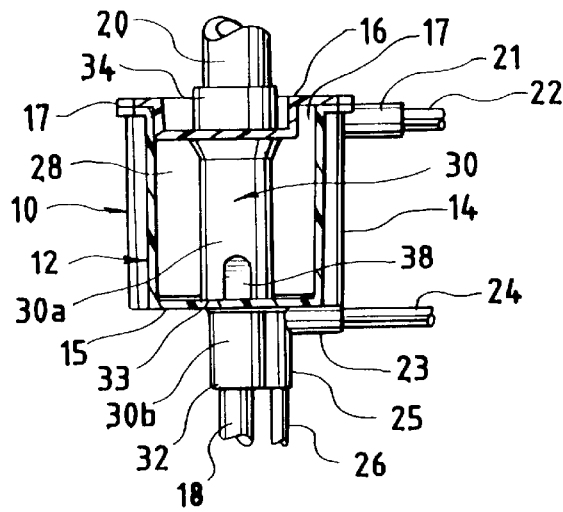
FIG. 2 is an elevational view taken partly in section along line 2—2 of FIG. 1, also showing connection of the chamber to other components of an otherwise conventional hemodialysis blood flow set.

As shown in FIG. 2, bubble trap 10 comprises a chamber defining wall 12 made of a cylindrical, cup shaped member 14 closed at one end 15, and closed at the other end with a cap 16, which is peripherally sealed to cup 14 about flange 17.

The bubble trap with its chamber defining wall 14 comprises a part of a blood handling set of any desired design, comprising flow tubing 18, roller pump tubing 20 of larger diameter than flow tubing 18, and various branch tubings 22, 24, 26, each of which communicates with the chamber interior 28. Tubing 22 may connect with a pressure monitor of conventional design. Tubing 24 may comprise a blood or other fluid access line. Tubing 26 may connect to a source of intravenous solution such as 0.9% saline or the like, to permit rapid and convenient administration of saline solution if and when needed.

Figure 3:
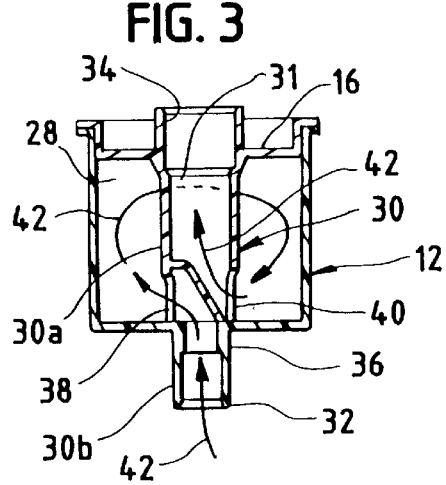
FIG. 3 is a sectional view taken along line 3—3 of FIG. 1.
Figure 4:
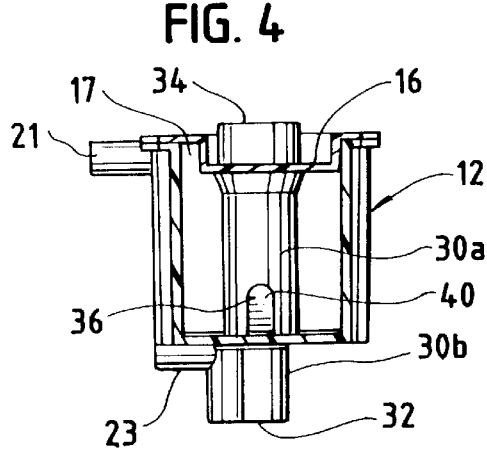
FIG. 4 is a sectional view taken along line 4—4 of FIG. 1.
Figure 6:
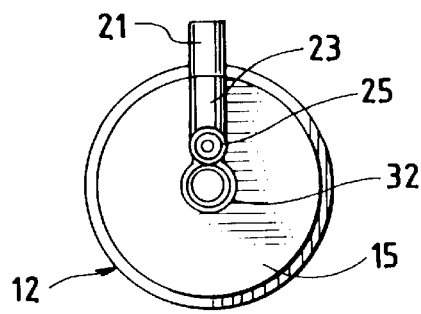
FIG. 6 is a bottom plan view of the bubble trap of this invention.
Figure 5:
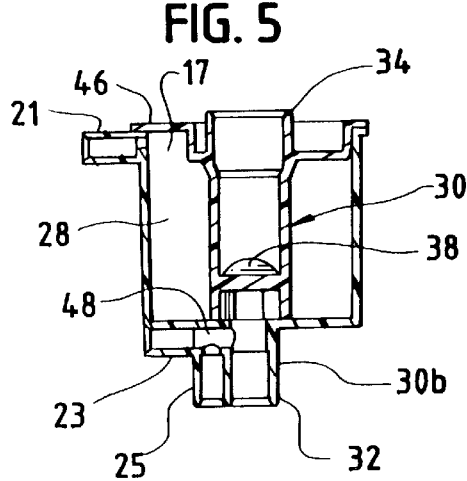
FIG. 5 is a sectional view taken along line 5—5 of FIG. 1.

Chamber wall 12 surrounds a two-component flow inlet/outlet tube 30, which extends completely through chamber 12 except for a possible gap at area 33, and is open at its opposed ends 32, 34. A first tube component comprises tube 30a which is attached to, and preferably comolded with, cap 16. A second, coaxial tube component comprises tube 30b which is integral with bottom wall 15 of cup-shaped member 14, and also may be comolded with that piece. When cap 16 is sealed to cup member 14, first tube 30a is positioned as shown in FIGS. 2–4. A small gap may be present between lower end 33 of first tube component 30a and bottom wall 15 so that the parts may be molded with relatively low tolerance and reliably sealed together without first tube component 30a being accidentally made too long, which would interfere with the sealing of cap 16 and cup member 14. A small amount of fluid leakage between the end 33 and bottom wall 15 is generally of little consequence.

End 32 comprises an aperture for conventional, sealed connection with flow tube 18 and tube component 30b. Tube end 34 may be of a different size to similarly seal with pump tubing 20.

Flow between set tubing 18 and roller pump tubing 20 does not proceed directly through the length of flow inlet/outlet tube 30, as is particularly illustrated by FIG. 3. The bore 31 of tube component 30a is closed by a diagonal partition 36, which extends diagonally along the length of the interior of tube component 30a and essentially separates and diverts tube inlet flow from outlet flow. A flow inlet port 38 is defined in the wall of tube component 30a within the chamber interior 28. A flow outlet port 40 is also defined in the wall of tube component 30a within chamber interior 28, with partition 36 essentially closing and separating the bore of tube 30 between inlet and outlet ports 38, 40. By the arrangement shown in FIG. 3, it is possible for ports 38, 40 to be at the same longitudinal position along the length of tube 30, but facing away from each other, while being separated by partition 36.

Thus, as indicated by the flow arrows 42, which illustrate a "prepump" arterial chamber installation, blood or other fluid can enter tube 30 at end 32 from set tubing 18. The flow passes out of flow inlet port 38 into chamber interior 28, circulating in the chamber interior 28 in a substantially horizontal, circumferential flow pattern around tube 30 until it reaches flow outlet port 40. Then, the flow reenters tube 30 through port 40 again on the other side of partition 36, and passes upwardly as shown by flow arrows 42 to exit the tube 30 from end 34 into the pump tubing 20. As this takes place, bubbles in the fluid can rise and be trapped against the lower surface of cap 16, and in bubble accumulating space 17, when tubing 30 occupies a substantially vertical position as shown, so that the bubbles are trapped and do not pass onwardly through flow outlet port 40.

It is to be understood that the bubble trap of this invention can operate in the opposite direction if desired, with the flow inlet coming through tube end 34 and the flow outlet exiting through tube end 32. In this case, the function of the flow ports 38, 40 is reversed, and the flow pattern is reversed, which can effectively take place in this design of chamber without a loss of bubble trapping capability. Tube 20 may also be a non-pump tube if desired, such as when chamber 10 is used as a venous chamber.

It can be seen that the auxiliary lines 22, 24, 26 are respectively connected to molded ports 21, 23, 25 in conventional, sealed manner to provide connection to chamber 12. Port 21 connects horizontally to the chamber interior 28 through aperture 46 (FIG. 5), permitting chamber 10 to fit snugly next to the roller pump housing of a hemodialyzer machine. Port 25 connects to a common channel 48 with port 23, which, in turn, connects to the interior of tube 30 adjacent to the end 32 of tube 30. Thus, communication is provided between all of the connecting lines and chamber interior 28.

The chamber interior 28 may have height of about 18–32 mm. (measured to the bottom of top wall 16) and an outer diameter of about 26–40 mm., to preferably give it a blood volume, including the volume of tube 30, of about 15–30 cc. Thus, a significant size reduction is achieved while the chamber still is highly effective at removing bubbles from blood at high flow rates.

The above has been offered for illustrative purposes only, and is not intended to limit the scope of the invention of this application, which is as defined in the claims below.

That which is claimed:

1. A flow-through bubble trap for fluid flow lines, which comprises:
   a chamber-defining wall, including top and bottom walls;
   a flow inlet/outlet tube at least substantially extending through said chamber and open at opposed tube ends to respectively define an inlet and an outlet of said bubble trap, said tube defining: a flow inlet port within the chamber interior adjacent to the bottom wall, a flow outlet port within the chamber interior adjacent to the bottom wall, said flow inlet and flow outlet ports facing laterally of said tube; and a flow-blocking partition closing the bore of said tube between said flow inlet and outlet ports; said bubble trap being constructed and arranged such that bubbles entering the inlet of said bubble trap are allowed to rise toward the top wall of said chamber.

2. The bubble trap of claim 1 in which said partition extends diagonally within said tube.

3. The bubble trap of claim 1 in which said chamber-defining wall is substantially circular in cross-section.

4. The bubble trap of claim 1 in which the chamber interior has a height that is substantially not greater than the longest horizontal dimension of said chamber interior.

5. The bubble trap of claim 4 in which the chamber interior has a height that is less than the longest horizontal dimension of said chamber interior.

6. The bubble trap of claim 1 in which said flow inlet/outlet tube comprises a pair of separate, substantially coaxial tube sections.

7. The bubble trap of claim 1 in which said flow inlet port faces away from said flow outlet port.

8. The bubble trap of claim 1 in which one end of said flow inlet/outlet tube is directly connected to a length of roller pump tubing.

9. The bubble trap of claim 8 in which said chamber-defining wall carries a supplemental inlet port communicating with the chamber interior at an end of said bubble trap adjacent to said roller pump tubing, said supplemental inlet port extending transversely to said flow inlet/outlet tube.

10. The bubble trap of claim 1 in which said flow inlet/outlet tube is spaced by at least 7 mm. from sidewall portions of said chamber-defining wall.

11. A tubular set for conveying blood between a patient and a blood treatment apparatus, said set comprising the flow-through bubble trap of claim 1 connected to other set tubing.

12. The bubble trap of claim 1 which has an internal volume of no more than about 25 ml.

13. A flow-through bubble trap for fluid flow lines, which comprises:
   a chamber-defining wall;
   a flow inlet/outlet tube at least substantially extending through said chamber and open at opposed tube ends to respectively define an inlet and an outlet of said bubble trap, said tube having a tube wall and defining: a flow inlet port within the chamber interior, a flow outlet port within the chamber interior, said flow inlet and said flow outlet ports facing laterally through said tube wall, and a flow-blocking partition closing the bore of said tube between said flow inlet and outlet ports, said inlet and outlet ports being positioned adjacent to a bottom wall portion of said chamber-defining wall and facing away from each other, said bubble trap being constructed and arranged such that bubbles entering the inlet of said bubble trap are allowed to rise towards the top of said chamber, said bubble trap having an interior volume of no more than about 25 ml.

14. The bubble trap of claim 13 in which the chamber interior has a height that is not substantially greater than the longest horizontal dimension of said chamber interior.

15. The bubble trap of claim 14 in which one end of said flow inlet/outlet tube is directly connected to a length of roller pump tubing.

16. The bubble trap of claim 15 in which said chamber-defining wall carries a supplemental inlet port communicating with a chamber interior at an end of said bubble trap adjacent to said roller pump tubing, said supplemental inlet port extending transversely to said flow inlet/outlet tube.

17. The bubble trap of claim 15 in which said flow inlet/outlet tube is spaced by at least 7 mm. from side wall portions of said chamber-defining wall.

18. The bubble trap of claim 15 in which said partition extends substantially longitudinally within said tube while also extending transversely to close said bore.

19. The bubble trap of claim 15 in which said flow inlet/outlet tube comprises a pair of separate, substantially coaxial tube sections.

20. A tubular set for conveying blood between a patient and a blood treatment apparatus, said set comprising the flow-through bubble trap of claim 13 connected to other set tubing.

21. A flow-through bubble trap for fluid flow lines, which comprises:

a chamber-defining wall comprising a cup-shaped chamber member having a bottom wall, said cup-shaped chamber member being closed by a peripherally sealed lid member at an end opposed to said bottom wall;

an open ended flow inlet/outlet tube comprising a first tube member extending centrally through said bottom wall and a second tube member extending centrally through said lid member, said first and second tube members extending substantially the length of said cup-shaped member in substantially coaxial relationship; laterally facing, spaced flow inlet and flow outlet ports defined by said first and second tube members within the chamber interior, said flow inlet and flow outlet ports being positioned adjacent to said bottom wall and facing away from each other, and a partition substantially closing the bore of at least one of said first and second tube members between said flow inlet and outlet ports to substantially block flow within the bore of said first and second tube members directly through said flow inlet/outlet tube.

22. The bubble trap of claim 21 in which the chamber interior has a height that is not substantially greater that the longest horizontal dimension of said chamber interior.

23. The bubble trap of claim 22 in which one end of either said first or second tube members is directly connected to a length of roller pump tubing.

24. The bubble trap of claim 23 in which said chamber-defining wall carries a supplemental inlet port communicating with the chamber interior at an end of said bubble trap adjacent to said roller pump tubing, said supplemental inlet port extending transversely to said flow inlet/outlet tube.

25. The bubble trap of claim 23 in which said first and second tube members are spaced by at least seven millimeters from side wall portions of said cup-shaped member.

26. A tubular set for conveying blood between a patient and a blood treatment apparatus, said set comprising the flow-through bubble trap of claim 21 connected to other set tubing.

27. The bubble trap of claim 21 which has an internal volume of no more than about 25 ml.

28. A flow-through bubble trap for fluid flow lines, which comprises:

a chamber having top, bottom, and side walls;

a first port tube communicating upwardly into said chamber; a second port tube communicating downwardly into said chamber, said port tubes arranged to define a direction of flow;

a flow-directing baffle system positioned to direct incoming fluid from one of said port tubes into a first lateral flow direction relative to the direction of flow within said port tubes, and to allow substantially horizontal flow circulation in said chamber, said baffle system also allowing fluid flow from circulating fluid in said chamber into the other of said port tubes in a lateral flow direction that is generally the same as said first lateral flow direction, while preventing direct flow between said first and second port tubes, said baffle system being positioned adjacent to the bottom wall of said chamber.

29. The bubble trap of claim 28 in which said first port tube communicates through said bottom wall and said second port tube communicates through said top wall, said port tubes being substantially in coaxial relation.

30. A tubular set for conveying blood between a patient and a blood treatment apparatus, said set comprising the flow-through bubble trap of claim 28 connected to other set tubing.

31. The bubble trap of claim 28 in which said chamber has an internal volume of no more than about 25 ml.

\* \* \* \* \*